US012422390B2

(12) United States Patent
Füglein et al.

(10) Patent No.: US 12,422,390 B2
(45) Date of Patent: Sep. 23, 2025

(54) DEVICE AND METHOD FOR A THERMAL ANALYSIS OF A SAMPLE

(71) Applicant: NETZSCH-Gerätebau GmbH, Selb (DE)

(72) Inventors: Ekkehard Füglein, Selb (DE); Georg Neumann, Schönwald (DE)

(73) Assignee: NETZSCH-Gerätebau GmbH, Selb (DE)

( * ) Notice: Subject to any disclaimer, the term of this patent is extended or adjusted under 35 U.S.C. 154(b) by 399 days.

(21) Appl. No.: 18/173,181

(22) Filed: Feb. 23, 2023

(65) Prior Publication Data
US 2023/0266259 A1 Aug. 24, 2023

(30) Foreign Application Priority Data
Feb. 24, 2022 (DE) .......................... 102022104400.9

(51) Int. Cl.
*G01N 25/48* (2006.01)
*B01L 3/04* (2006.01)
(52) U.S. Cl.
CPC ................ *G01N 25/48* (2013.01); *B01L 3/04* (2013.01); *B01L 2300/044* (2013.01); *B01L 2300/0672* (2013.01); *B01L 2300/18* (2013.01)
(58) Field of Classification Search
CPC ..... G01N 25/48; B01L 3/04; B01L 2300/044; B01L 2300/0672
See application file for complete search history.

(56) References Cited

U.S. PATENT DOCUMENTS 4,739,699 A * 4/1988 Nelson et al. ............ A23L 3/00
99/468
7,282,184 B2 * 10/2007 King et al. ............... B01J 19/00
422/130
(Continued)

OTHER PUBLICATIONS

Piro et al., "Exploring Crucible Designs for Differential Scanning Calorimetry Measuring of Fluoride Salts", Elsevier, Jan. 2021, pp. 1-14 (Year: 2021).*

*Primary Examiner* — John E Breene
(74) *Attorney, Agent, or Firm* — Whitmyer IP Group LLC

(57) ABSTRACT

A thermal analysis of samples and proposes a device for a thermal analysis of a sample, having: a sample chamber for receiving a sample crucible including a crucible cover attached thereto, in the interior of which a sample to be analyzed is located, wherein the sample chamber has a chamber opening for introducing the sample crucible into the sample chamber; a temperature control mechanism for controlling the temperature of the sample chamber; a measuring mechanism for measuring a temperature of the sample and one or several further measured variables; a gas conveying mechanism for creating a gas atmosphere in the sample chamber; a chamber cover, which can be attached to the chamber opening of the sample chamber; and a piercing mechanism equipped with a needle, which is suitable to pierce a hole into the crucible cover of the sample crucible by means of the needle when the sample crucible is received in the sample chamber and when the chamber cover is attached to the chamber opening. A corresponding method for a thermal analysis of a sample, a sample crucible including a crucible cover, as well as a covering/piercing unit are further proposed as part of the invention.

15 Claims, 5 Drawing Sheets

(56) References Cited

U.S. PATENT DOCUMENTS

| | | | |
|---|---|---|---|
| 2005/0123020 A1* | 6/2005 | Kakamura | G01N 25/00 374/14 |
| 2011/0226046 A1* | 9/2011 | Giardino et al. | G01N 3/48 73/82 |
| 2013/0040400 A1* | 2/2013 | Konings et al. | G01N 23/04 436/164 |
| 2016/0047779 A1* | 2/2016 | Olson et al. | G01N 29/022 |
| 2019/0284612 A1* | 9/2019 | Buse et al. | C12Q 1/6806 |
| 2019/0308191 A1* | 10/2019 | Hart et al. | B01L 3/00 |
| 2020/0147515 A1* | 5/2020 | Okado | B01D 11/02 |
| 2020/0278368 A1* | 9/2020 | Hopper | G01N 35/1009 |
| 2020/0353467 A1* | 11/2020 | Cappi et al. | B01L 3/502715 |

* cited by examiner

DEVICE AND METHOD FOR A THERMAL ANALYSIS OF A SAMPLE

TECHNICAL FIELD

The present invention relates to a device as well as a method for a thermal analysis of a sample. The invention further relates to a sample crucible, which can be used thereby, comprising a crucible cover, as well as a covering/piercing unit, which can be used for a device of this type.

BACKGROUND

Devices for the thermal analysis of a sample are known in a large variety of embodiments from the prior art and have a sample chamber for receiving (at least) one sample to be analyzed or for receiving (at least) one sample crucible, in the interior of which the sample to be analyzed is located. The devices furthermore have a temperature control mechanism for controlling the temperature of the sample chamber as well as a measuring mechanism for measuring a temperature of the sample and one or several further measured variables.

Methods for the thermal analysis can advantageously be used, e.g., to characterize material properties (e.g., specific heat capacity, heat conductivity, melting, decomposition, and crystallization temperatures), including, e.g., the properties of the processes, which take place as a function of temperature or during temperature change, respectively (e.g., enthalpies during phase transitions or chemical reactions, etc.).

Examples for methods for the thermal analysis are, e.g., the thermogravimetry (TG), the differential thermal analysis (DTA), as well as the differential scanning calorimetry (DSC) derived therefrom.

In the case of the methods, which are of particular interest in the context of the invention, the temperature of the sample is typically controlled according to a temperature program, in the course of which a chamber temperature in the interior of the sample chamber is changed, and the sample temperature and additionally one or several further measured variables of the sample are measured simultaneously relating to properties of the sample by means of the measuring mechanism.

For example, the weight or the mass of the sample, respectively, is measured in the course of a temperature program as such a "property of the sample" in the case of the thermogravimetry (TG).

Depending on the concrete embodiment of the measuring mechanism, a plurality of measurements of further physical variables can generally be provided during the thermal analysis in addition to a measurement of the sample temperature and, e.g., of the sample mass, in the course of the temperature program.

One example for this is the determination of the temperature-dependent caloric effects of a sample by means of DSC with simultaneous determination of the temperature-dependent mass of the sample by means of thermogravimetry (TG). A further example is the determination of the type and quantity of volatile decomposition products of a sample in the course of the temperature program by means of mass spectroscopy (MS) with simultaneous determination of the temperature-dependent mass of the sample by means of thermogravimetry (TG). A thermal analysis while simultaneously using several different methods is also referred to here as "simultaneous thermal analysis".

In this respect, the term "properties of the sample" (measured by the measuring mechanism), which is used here, is to thus be understood very broadly and can comprise, e.g., the above-mentioned "type and quantity" of volatile decomposition products.

In the case of certain materials and samples produced therefrom, the problem arises that the samples can be contaminated by components of the atmosphere, such as, e.g., oxygen, carbon dioxide, water (humidity), etc., and/or can chemically react with components of this type, so that the respective samples are changed in an undefined manner thereby.

With regard to storage and/or transport of a sample, a simple solution of the problem is to "package" the sample immediately after the production thereof in a sample crucible comprising an air-tight crucible cover attached thereto, or to produce the sample in a sample crucible, and to immediately provide this crucible with the air-tight crucible cover thereby.

However, the above-mentioned risk of contamination and/or chemical reaction also remains in the case of a sample, which is located in a sample crucible comprising an air-tight crucible cover attached thereto, as soon as the sample is introduced into the device as part of a so-called "sample preparation", and the crucible cover has to be removed or opened otherwise in preparation for the thermal analysis, which is absolutely necessary in the case of many thermal analyses.

A possible solution of this problem is to introduce the sample crucible, which is still closed in an air-tight manner, into a chamber (so-called "glove box"), which is closed in an air-tight manner, together with the device, and to then perform the sample preparation and performance of the thermal analysis in this chamber under vacuum or under a protective gas atmosphere.

Apart from this solution, which is highly complex and rather unpracticable for cost reasons, the problem can be somewhat alleviated by using a sample crucible comprising a crucible cover, which does not have to be removed completely (e.g. unscrewed) during the sample preparation, but in the case of which only a small hole can be pierced, e.g. by means of a needle, in order to thus create a medium-permeable connection between the interior of the sample crucible and the sample chamber of the device for the following thermal analysis.

In the case of this approach, however, e.g., the "puncturing" of the crucible cover in ambient air, a certain risk of contamination and/or chemical reaction with components of the ambient air remains when introducing the sample into the device.

SUMMARY

In the case of a device and a method for a thermal analysis, it is an object of the present invention to reduce the risk, which exists as part of a sample preparation, of a change of the sample as a result of unwanted chemical or physical reactions.

According to a first aspect of the invention, this object is solved by means of a device for a thermal analysis of a sample, having
 a sample chamber for receiving a sample crucible comprising a crucible cover attached thereto, in the interior of which a sample to be analyzed is located, wherein the sample chamber has a chamber opening for introducing the sample crucible into the sample chamber, a temperature control mechanism for controlling the temperature of the sample chamber, a measuring mechanism for measuring a temperature of the sample and one or several further measured variables, a gas conveying mechanism for creating a gas atmosphere in the sample chamber, a chamber cover, which can be attached to the chamber opening of the sample chamber, a piercing mechanism equipped with a needle, which is suitable to pierce a hole into the crucible cover of the sample crucible by means of the needle when the sample crucible is received in the sample chamber and when the chamber cover is attached to the chamber opening.

With the invention, it is possible in an advantageous manner to drastically reduce the risk of an unwanted change of the sample as a result of chemical or physical reactions with components of the ambient air because the sample crucible can be introduced in the closed state into the sample chamber and can be opened there under a defined gas atmosphere.

In a preferred embodiment of the invention, it is provided that the gas atmosphere created in the sample chamber contains at least one gas, which is selected from the group consisting of nitrogen, argon, and helium. With regard to its purpose, a gas atmosphere of this type can also be referred to as inert gas atmosphere or protective gas atmosphere.

In the case of many conventional devices and methods of thermal analysis, it is already provided that a so-called carrier gas flows through the sample chamber while performing the thermal analysis, in order to discharge gaseous substances released by the sample (e.g. volatile components or volatile reaction products) in a defined manner and to supply them to an analysis unit of the measuring device, such as, e.g., a gas chromatography/mass spectroscopy mechanism.

It can be provided in this case that at least a portion (e.g., gas source, gas inlet, etc.) of the means for creating a carrier gas flow in the sample chamber is used additionally to create the gas atmosphere in the sample chamber in the course of the sample preparation. The compositions of the gases during the sample preparation ("protective gas") on the one hand, and when performing the thermal analysis ("carrier gas") on the other hand, can be selected to be identical or to differ from one another.

In one embodiment of the invention, it is provided that the chamber cover and the piercing mechanism are formed to be structurally combined as a covering/piercing unit.

For many device designs, which are already in use, this has the advantage that the invention can be realized by means of a rather slight modification to the design and thus in a simple and cost-efficient manner.

In a further development of this embodiment, it is provided that the device has a further chamber cover, which can be attached, instead of the covering/piercing unit, to the chamber opening of the sample chamber.

This further development is highly advantageous, e.g., in particular when, apart from the function of protecting an exchange of media and/or energy (heat) between sample chamber and environment, the chamber cover has at least one further function when performing the thermal analysis. This is so because, according to this further development, the covering/piercing unit can be replaced with a chamber cover, which is optimized with regard to the mentioned further function(s), after piercing the hole into the crucible cover and before performing the thermal analysis of the sample. Such a further function can be, e.g., to provide a gas outlet, through which gas acting as carrier gas during the thermal analysis of the sample, together with gaseous components originating from the sample, can be transferred out of the sample chamber to an analysis unit of the measuring device (e.g., gas chromatography/mass spectroscopy mechanism).

In another further development of this embodiment, it is provided that the covering/piercing unit has a gas outlet (e.g., at least a small opening), through which gas can flow from the gas atmosphere of the sample chamber to the outside into the environment when the covering/piercing unit is attached to the chamber opening.

A quick and complete displacement of air from the sample chamber can be attained in an advantageous manner by means of this further development immediately after attachment of the covering/piercing unit, in that the creation of the gas atmosphere is realized by means of a gas throughflow of the sample chamber, which is effected by means of the gas conveying mechanism, during which gas is allowed to flow into the sample chamber, e.g. at a location, which is relatively far from the chamber opening, and is allowed to flow out at said gas outlet of the covering/piercing mechanism.

When the hole is then pierced into the crucible cover at this stage of the sample preparation (and gas thereby preferably continues to flow), and the covering/piercing unit is subsequently removed from the chamber opening of the sample chamber (in order to replace it with another chamber cover before performing the thermal analysis), the gas flowthrough of the sample chamber in this direction, i.e. from the interior of the device to the chamber opening of the sample chamber, prevents or minimizes, respectively, an entrance of ambient air into the sample chamber in an advantageous manner.

The covering/piercing unit can have, e.g., a wall provided for covering the chamber opening and a guide bearing formed on the wall for movably storing the needle, wherein the needle can extend from an inside of the wall, which faces the sample chamber when the covering/piercing unit is attached, through the wall, to an outside of the wall, which faces away from the sample chamber when the covering/piercing unit is attached.

In the latter case, it can be provided, e.g., that a "drive of the needle" provided for the piercing process is accomplished by means of a mechanical impact (push) on the section of the needle located on the outside of the wall. This has the advantage, e.g., that corresponding drive components inside the sample chamber are not required for driving the needle. On the contrary, these drive components can be arranged on the outside of the covering/piercing unit without impacting the sample chamber and without installation space problems.

If a vertical piercing movement of the needle from the top to the bottom is thereby provided in the use situation of the device, for example a manually operable and thus very simple embodiment of a covering/piercing unit can in particular be of interest in many cases, which has a wall provided for covering the chamber opening and a guide bearing formed on the wall for movably storing the needle, wherein the needle extends from the above-mentioned inside of the wall through the wall to the above-mentioned outside of the wall, and wherein the covering/piercing unit further has a weight, which is vertically movably guided on the covering/piercing unit, which can be dropped from a predetermined height with respect to the needle onto a distal end of the needle or another point on the needle by means of a manual operating action by a user.

Alternatively, to a manual operating action, by means of which such a weight can be lifted to the predetermined height and can then be dropped, it is also possible to equip the piercing mechanism or the covering/piercing unit, respectively, with a motor-driven mechanism, which is suitable for this purpose.

Alternatively, to the use of a falling weight, by means of which a relatively quick piercing movement of the needle is effected, which is generally advantageous, it is also possible to provide a motor-driven mechanism, which acts on the needle via a gear connection, in order to drive the piercing movement of said needle. With an embodiment of this type, it is in particular also possible to provide a relatively slow piercing movement of the needle.

An optimal piercing movement (e.g., quick or slow, with short or long stroke), as well as, e.g., an optimal design of a needle piercing the crucible cover and thereby in particular of the tip thereof, can be determined, e.g., empirically, depending on the application (design of the crucible cover).

In the case of one embodiment, the needle has a rotationally symmetrical shape (e.g., cylindrical shaft with conical tip) at least in the region of its tip and an adjoining shaft region. In the case of a conical needle tip, an angle defined from the needle tip, viewed in the side view, can lie, e.g., in a range of 5° to 60°, in particular 10° to 30°.

In one embodiment of the invention, it is provided that the piercing mechanism has a mechanical stop for limiting a piercing depth of the needle. Alternatively, or additionally, it can be provided, e.g., that the piecing mechanism has a spring mechanism, which biases the needle opposite to its piercing direction, whereby a defined piercing depth can likewise be attained, e.g., in the case of the above-mentioned embodiment with a falling weight.

In one embodiment of the invention, it is provided that the piercing mechanism has a mechanical centering mechanism for centering the sample crucible together with the crucible cover with respect to the needle.

The centering mechanism can have, e.g., two or more centering jaws for contacting a jacket surface of the sample crucible or the crucible cover attached thereto, in order to thus force the sample crucible together with the crucible cover into a certain position with respect to the needle (centering), before the hole is pierced into the crucible cover of the sample crucible by means of the needle of the piercing mechanism.

In one embodiment of the invention, it is provided that a crucible receptacle comprising a deposit surface for depositing the sample crucible thereon is formed in the sample chamber, wherein the crucible receptacle can be displaced between a first position for depositing the sample crucible and piercing a hole into the crucible cover, and a second position for performing the thermal analysis of the sample.

The second position of the displaceable crucible receptacle is thereby preferably provided further away from the chamber opening and/or "further inside the device" than the first position.

In a more specific embodiment, a displaceability of the crucible receptacle is provided in the vertical direction, wherein the second position is provided further away from the chamber opening and/or "further inside the device" than the first position.

Even though displaceable crucible receptacles are often also provided in the case of devices known from the prior art, they predominantly only serve the purpose there to simplify an introduction and depositing of the sample crucible, which is held, e.g., by means of a pair of tweezers, into the device (for instance through a relatively small chamber opening of the sample chamber), whereby it should be taken into consideration that the sample has to generally be located in a position "further inside" the device during the following analysis in order to ensure the most precise temperature control of the sample, which is to be analyzed, in the sample chamber.

In the context of the present invention, however, the above-mentioned displaceable crucible receptacle provides, e.g., the additional advantage that the structural realization of the piercing mechanism, either structurally combined with the chamber cover (as covering/piercing unit) or separately from the chamber cover, becomes easier.

The above-mentioned displaceable crucible receptacle further makes it possible that (in the case of a corresponding design) mechanical stresses caused by piercing the hole into the crucible cover of the sample crucible can be kept away from mechanically sensitive components of the device, for example a scale provided for the thermogravimetric analysis (TG).

A further advantage of the embodiment comprising a displaceable crucible receptacle follows for the case that the device has a further chamber cover, which, instead of a covering/piercing unit, can be attached to the chamber opening of the sample chamber. This is so because it can be provided in this case that the sample crucible, together with the crucible cover, which has already been punctured, is displaced from the first position (for depositing the sample crucible and puncturing the crucible cover) into a second position, which is provided "further inside" (e.g. lowered into the device) with respect to the first position or which is provided at least further away from the chamber opening, before (in the second position of the crucible receptacle) the covering/piercing unit is then removed from the chamber opening of the sample chamber and is replaced with the other chamber cover.

Due to the fact that the sample crucible in the second position is located further inside or at least further away from the chamber opening, respectively, on which a certain exchange can take place between gas atmosphere and ambient air after the removal of the covering/piercing unit, the sample is particularly well protected against a contact with ambient air during this phase (replacement of the chamber cover).

It is important to also point out once again in this context that the protective gas flowthrough of the sample chamber, which has been mentioned further above, from the interior of the device to the chamber opening of the sample chamber already effects a protection of the sample against a contact with ambient air. This protection, however, can be increased further in an advantageous manner by means of the displacement of the sample crucible (comprising the already punctured crucible cover) from the first position into the second position and thus further away from the chamber opening.

According to a further aspect of the invention, the above-posed object is solved by means of a method for a thermal analysis of a sample, which is located in the interior of a sample crucible comprising a crucible cover attached thereto, in particular by using a device of the type described here, wherein the method comprises the following steps:
  introducing the sample crucible into the sample chamber through a chamber opening of a sample chamber,
  attaching a chamber cover to the chamber opening of the sample chamber and creating a gas atmosphere in the sample chamber by means of a gas conveying mechanism, piercing a hole into the crucible cover of the sample crucible by means of a piercing mechanism, performing the thermal analysis of the sample by means of a temperature control mechanism for controlling the temperature of the sample chamber and a measuring mechanism for measuring a temperature of the sample and one or several further measured variables.

The embodiments and special designs described here for the device according to the invention can also be provided analogously, either individually or in any combination, as embodiments or special designs, respectively, of the method according to the invention, and vice versa.

In one embodiment, it is provided that the chamber cover and the piercing mechanism are formed to be structurally combined as a covering/piercing unit, wherein the covering/piercing unit is removed from the chamber opening of the sample chamber after piercing the hole into the crucible cover and before performing the thermal analysis of the sample and is replaced with another chamber cover.

In a further development of this embodiment, it is provided that the creation of the gas atmosphere is realized by means of a gas flowthrough of the sample chamber, which is effected by means of the gas conveying mechanism and the flow rate of which is higher while replacing the covering/piercing unit with the other chamber cover than while performing the thermal analysis.

In one embodiment of the method, it is provided that a crucible receptacle, which can be displaced between a first position and a second position, is formed in the sample chamber, and that the introduction of the sample crucible into the sample chamber takes place by depositing the sample crucible on a deposit surface of the crucible receptacle when the crucible receptacle is in the first position, after the chamber cover is attached to the chamber opening of the sample chamber and after the gas atmosphere is created in the sample chamber, the piercing of the hole into the crucible cover takes place when the crucible receptacle is in the first position, after piercing the hole into the crucible cover and before performing the thermal analysis of the sample, a displacement of the crucible receptacle from the first position into the second position takes place.

The second position of the displaceable crucible receptacle is thereby preferably provided further away from the chamber opening and/or further inside the device than the first position. The displacement of the crucible receptacle can in particular take place in the vertical direction, wherein the second position is provided further away from the chamber opening and/or further inside the device (e.g., lower) than the first position.

In a further development, it is provided that the device has a further chamber cover, which, instead of a covering/piercing unit, can be attached to the chamber opening of the sample chamber, and that the removal of the covering/piercing unit from the chamber opening and the replacement thereof with the other chamber cover takes place when the crucible receptacle is in the second position.

According to a further aspect of the invention, a sample crucible comprising a crucible cover is proposed, which is formed in a special way for a use for a device and/or in a method of the type described here, and which has, for this purpose:

an at least approximately cylindrically shaped sample crucible comprising an interior for receiving the sample and comprising a crucible opening, a crucible cover, which can be or is attached to the sample crucible at the crucible opening of the sample crucible, wherein the crucible cover has:

a cap, in particular screw cap, which can be or is connected to an opening edge of the sample crucible, comprising a cap hole formed therein, a pierceable sealing layer, which seals the interior of the sample crucible, and which is arranged on the inside of the cap.

In the case of a sample crucible of this type comprising a crucible cover, the piercing of a hole into the crucible cover, which is provided according to the invention, can advantageously take place in such a way that the needle used for this purpose passes through the cap hole and then pierces through the sealing layer located therebelow.

The cross sections of the cap hole on the one hand and of the needle on the other hand are to therefore be selected adapted to one another so that the needle or at least a tip of the needle, respectively, fits through the cap hole. In one embodiment, an opening surface of the cap hole is greater by at least a factor of 2, in particular by a factor of 4, than a maximum cross-sectional surface of a section of the needle or needle tip, respectively, which is located in the region of the cap hole during the piercing process. On the other hand, it is favorable for the most part when this opening surface of the cap hole is greater by a factor of 10 than this maximum cross-sectional surface of the needle (tip).

A material and a thickness of the sealing layer on the one hand, and a material and a shape of the needle on the other hand are to be selected adapted to one another so that the material of the sealing layer can be penetrated by means of the needle, and a hole can thus be pierced into the sealing layer.

Material and shape (in particular, e.g., thickness) of the cap can advantageously be selected independently of the design of the needle, depending on the desired mechanical stability of the cap because the needle passes through the cap in the region of the cap hole, which is formed, for example, as a suitably dimensioned bore, during the piercing process.

The sample crucible can have a crucible body, which has at least approximately the shape of a bowl or of a pot.

In one embodiment, the sample crucible is made of a metal or a metal alloy, such as, e.g., steel, or, e.g., tungsten, titanium, or aluminum (or an alloy thereof), wherein surfaces limiting the interior of the sample crucible can be coated, for example. In particular precious metals or precious metal alloys, such as, e.g., gold or a gold alloy, respectively, are possible as material for such a coating.

In one embodiment, it is provided that the sample crucible has a circular bottom comprising a cylindrical or conical jacket, which adjoins upwardly in the use situation. The bottom and the jacket can thereby be formed, e.g., so as to be connected to one another in one piece. The crucible opening of the sample crucible is defined by an upper edge of the jacket in this case.

The sample crucible can have, e.g., a maximum lateral expansion in the range of 5 to 15 mm and/or a height in the range of 5 to 15 mm, preferably in a lateral expansion/height radio in the range of 1.0 to 1.5. A wall thickness of the crucible body can lie, e.g., in the range of 0.5 to 1 mm.

As already mentioned, the crucible cover, which can be or is attached, respectively, to the sample crucible at the crucible opening of the sample crucible, has at least one cap and, therebelow (towards the interior of the sample crucible), a pierceable sealing layer. In one embodiment, the cap is made of a metal material (metal or metal alloy), such as, e.g., steel, titanium, or aluminum (e.g., of the same material as the sample crucible).

In one embodiment, it is provided that the cap is formed as a screw cap comprising a thread (internal or external thread), which can be screw-connected to a corresponding thread (external or internal thread, respectively) of the sample crucible in the region of the crucible opening.

In one embodiment, the pierceable sealing layer, which seals the interior of the sample crucible, and which is arranged on the inside of the cap, is formed as a film made of a metal material. For example, in particular gold or a gold alloy is possible in an advantageous manner as material for the sealing layer. A thickness of the sealing layer can lie, e.g., in the range of 50 to 200 μm.

To realize the sealing effect, it can be provided, e.g., that an edge of the sealing layer is pushed circumferentially from the cap onto an upper edge region of the sample crucible, in other words is clamped between cap and sample crucible.

In an advantageous further development, it is provided that the crucible cover further has a stabilizing layer arranged on the inside of the sealing layer comprising a stabilizing layer hole, which is formed coaxially to the cap hole therein.

It can be provided in this case, e.g., that an edge of the two-layer structure of sealing layer and stabilizing layer arranged therebelow is clamped circumferentially between cap and sample crucible in order to realize the sealing of the interior of the sample crucible.

In the case of this further development, a mechanical support of the sealing layer is created in an advantageous manner by means of the stabilizing layer, so that the sealing layer cannot move back when being stressed with the needle when piercing the hole into the crucible cover (piercing the sealing layer), and a better-defined and reproducible geometry of the pierced hole is thus attained.

Due to the arrangement, which is provided coaxially to the cap hole and thus coaxially to the needle during the piercing process, of the stabilizing layer hole in the stabilizing layer, it is advantageously avoided that the piercing movement of the needle is impeded by the stabilizing layer.

In one embodiment, an opening surface of the stabilizing layer hole is greater by at least a factor of 2, in particular by a factor of 4, than a maximum cross-sectional surface of a section of the needle or needle tip, respectively, which is located in the region of the stabilizing layer hole during the piercing process.

In one embodiment of the device according to the invention, this device comprises at least one sample crucible together with a crucible cover of the type described here.

According to a further aspect of the invention, a covering/piercing unit for a device for a thermal analysis of a sample is proposed, wherein the device has a sample chamber for receiving a sample crucible comprising a crucible cover attached thereto, in the interior of which a sample to be analyzed is located, and wherein the sample chamber has a chamber opening for introducing the sample crucible into the sample chamber, wherein the covering/piercing unit has: a wall provided for covering the chamber opening; a guide bearing formed on the wall; and a needle, which is movably stored by means of the guide bearing and which extends from an inside of the wall facing the sample chamber when the covering/piercing unit is attached, through the wall, to an outside of the wall facing away from the sample chamber when the covering/piercing unit is attached.

In the case of a covering/piercing unit of this type according to the invention, in particular special embodiments and designs can be provided, as they have already been described here in connection with the device according to the invention.

According to a further aspect of the invention, a use of a device of the type described here and/or of a method of the type described here for performing one or several thermal analyses of a sample is proposed, selected from the group consisting of thermogravimetric analysis (TG), differential thermal analysis (DTA), and differential scanning colorimetry (DSC).

In one embodiment of this use, a simultaneous thermal analysis comprising one of the afore-mentioned analysis methods and at least one further analysis method is provided.

In an advantageous more specific embodiment, the use for a thermal analysis comprising a determination of the mass of a sample in the course of a temperature program by means of thermogravimetry (TG) and a simultaneous determination of the type and quantity of volatile decomposition products of the sample in the course of this temperature program by means of mass spectroscopy (MS or GC-MS, respectively), is provided.

In one embodiment of the invention, the temperature program defines a temperature in the interior of the sample chamber (chamber temperature), for which the method can comprise, e.g., a measuring of the chamber temperature and, based thereon, a control of the temperature control mechanism, preferably with a regulation (e.g., PID regulation) of the chamber temperature.

Deviating from this, the temperature program can alternatively also define a predetermined temporal course of the sample temperature, for the purpose of which the corresponding control (in particular regulation) of the temperature control mechanism can take place accordingly, e.g., based on the measured sample temperature.

Depending on the concrete embodiment of the method or of a measuring mechanism used thereby respectively, one or several further measured variables of the sample, in particular, e.g., measured variables relating to properties of the sample, are measured. For example, when using the method of thermogravimetry (TG), the weight or the mass of the sample, respectively, is measured as further measured variable in the course of a temperature change or of a temperature program, respectively.

Alternatively, or additionally, a further measured variable can refer, e.g., to type and/or quantity of volatile products (e.g., determined with the help of gas chromatography and/or mass spectroscopy), and/or can comprise at least one further temperature and/or temperature difference (e.g., with DSC). The method preferably comprises a recording of measuring data in the course of the temperature program, in particular of data, which represents the temperature-dependent and/or time-dependent course of at least one temperature of chamber temperature and sample temperature (preferably both). By evaluating data of this type during the temperature control and/or after conclusion of the temperature program, e.g. one or several material parameters of interest of the sample, which was subjected to the method, can be determined.

BRIEF DESCRIPTION OF THE DRAWINGS

The invention will be further described below on the basis of exemplary embodiments with reference to the enclosed drawings, in which.

DETAILED DESCRIPTION

Figure 1:
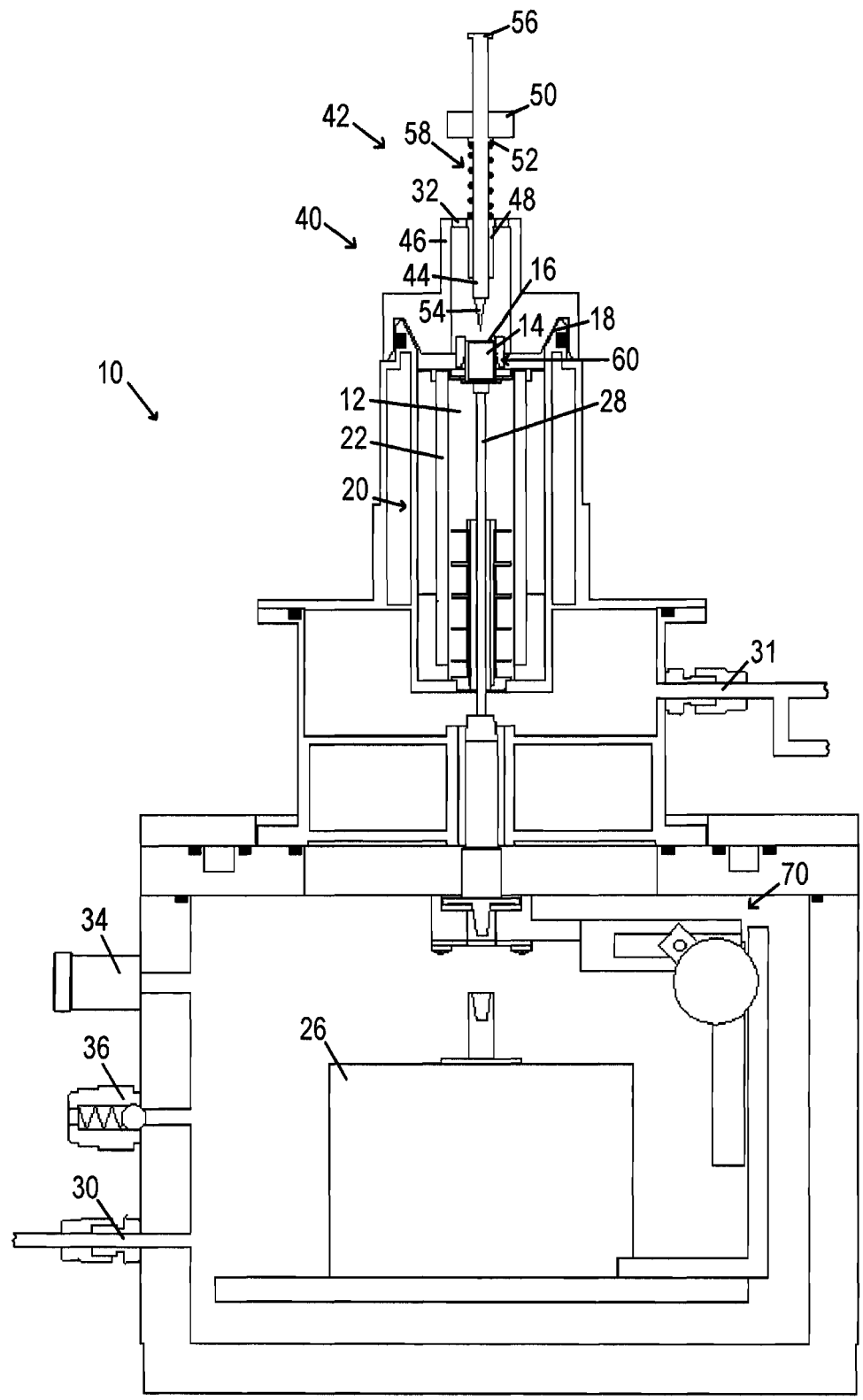
FIG. 1 shows a sectional view of a device for a thermal analysis of a sample according to an exemplary embodiment.

FIG. 1 shows an exemplary embodiment of a device 10 for a thermal analysis of a sample. The device 10 has a sample chamber 12 for receiving a sample crucible 14 comprising a crucible cover 16 attached thereto. During the thermal analysis, the sample to be analyzed is located in the interior of the sample crucible 14.

In an upper region of the device 10, the sample chamber 12 has a chamber opening 18, through which the sample crucible 14 can be introduced into the sample chamber 12 for preparing the analysis.

The device 10 further has a temperature control mechanism 20, by means of which the temperature of the sample chamber 12 and thus the sample located in the sample crucible 14 is controlled during the analysis of the sample. In the illustrated example, the temperature control mechanism 20 has a hollow cylindrical heating jacket 22 (e.g., electrical resistance heater).

In the illustrated exemplary embodiment, the device 10 is formed to perform a method for the thermal analysis of the sample, during which the temperature of the sample is controlled according to a predetermined temperature program, in the course of which a chamber temperature in the interior of the sample chamber 12 is changed, wherein a sample temperature and additionally one or several further measured variables relating to properties of the sample are measured in the course of the temperature program by means of a measuring mechanism of the device 10.

In the illustrated exemplary embodiment, a thermogravimetric analysis (TG) is provided during the thermal analysis of the sample, during which the change of the mass of the sample is measured (as further measured variable) in the course of the temperature program.

In the illustrated exemplary embodiment, the measuring mechanism thus comprises, in addition to a temperature measuring mechanism for measuring the sample temperature, in particular a scale 26, by means of which the weight of the sample together with the components provided for receiving and storing the sample on the scale 26 is measured. In the example, these components comprise, e.g., the sample crucible 14 together with crucible cover 16 and a sample crucible carrier 28. By means of an evaluation of the weight measured by means of the scale 26 in the course of the temperature program, the temperature-dependent change of the mass of the sample is attained.

To create a defined gas atmosphere or gas flowthrough, respectively, in the sample chamber 12, the device 10 has a gas conveying mechanism, which, in the illustrated exemplary embodiment, in particular has a gas inlet 30 arranged in a lower region of the sample chamber 12. In the illustrated example, a further gas inlet 31 is arranged in the lower region of the sample chamber 12. A gas (e.g., nitrogen, argon, or helium, or a mixture containing at least one inert gas of this type) can be allowed to flow into this region of the sample chamber 12 via these gas inlets 30, 31.

In the illustrated example and in the situation illustrated in FIG. 1, the gas conveying mechanism further has a gas outlet 32, which is arranged in the upper region of the sample chamber 12 and via which the protective gas can be allowed to flow out in this region of the sample chamber 12. In the example, the gas conveying mechanism of the device 10 furthermore has a pressure sensor 34 for measuring a pressure in the sample chamber 12 as well as an overpressure outlet valve (safety valve) 36, which let gas out of the sample chamber 12 in the case of an excessive pressure.

To cover the sample chamber 12 of the device 10 in a gas-tight manner to the top against the atmosphere (ambient air) when performing the thermal analysis, the device 10 further has one or several chamber covers, which can (optionally) be attached to the chamber opening 18 of the sample chamber 12. In the situation illustrated in FIG. 1, such a chamber cover 40 is attached to the chamber opening 18.

A special characteristic of the device 10 is that the sample crucible 14 can be introduced into the sample chamber 12 when being closed in an air-tight manner by means of the crucible cover 16 and can be opened there under gas atmosphere created by means of the gas conveying mechanism, in order to reduce the risk of an unwanted change of the sample as a result of chemical or physical reactions with components of the ambient air.

For this purpose, the device 10 further has a piercing mechanism 42, which, equipped with a needle 44 (e.g. made of steel or another metal alloy), is formed to use the needle 44 to pierce a hole into the crucible cover 16 of the sample crucible 14 when the sample crucible 14 is received in the sample chamber 12 and when the chamber cover 40 is attached to the chamber opening 18.

In the illustrated example, the chamber cover 40 and the piercing mechanism 42 are formed to be structurally combined as a covering/piercing unit 40, 42, and a situation is illustrated in FIG. 1, in which, after the introduction of the sample crucible 14 through the chamber opening 18 into the sample chamber 12, the covering/piercing unit 40, 42 was attached to the chamber opening 18.

In this situation, said hole can be pierced into the crucible cover 16 of the sample crucible 14 by means of the needle 44.

In the illustrated exemplary embodiment, the covering/piercing unit 40, 42 has a wall 46, which serves to cover the chamber opening 18, and a guide bearing 48 (slide bearing) formed on the wall 46 for movably storing the needle 44. The needle 44 thereby extends from an inside of the wall 46 facing the sample chamber 12 when the covering/piercing unit 40, 42 is attached, through the wall 46 to an outside of the wall 46 facing away from the sample chamber 12 when the covering/piercing unit 40, 42 is attached.

In the illustrated example, a "drive of the needle" provided for the piercing process is accomplished by means of a mechanical force on the section of the needle 44 located on the outside of the wall 46.

For this purpose, the piercing mechanism 42 has a weight 50, which is guided in a vertically movable manner, and which can be dropped by means of a manual operating action of a user from a predetermined height with respect to the needle 44 onto a radial protrusion 52 of the needle 44 formed on the shaft of the needle 44, in order to thus drive the needle 44 in FIG. 1 downwards, and to allow said hole to be pierced into the crucible cover 16 by means of a needle tip 54 of the needle 44.

To predetermine the height, from which the weight 50 is dropped onto the radial protrusion 52 of the needle 44, a further radial protrusion 56 is formed, e.g., on the shaft of the needle 44 in the illustrated example. During the previously mentioned manual operating action, the user can initially lift the weight 50 guided on the shaft of the needle 44, until it reaches the further radial protrusion 56, which thereby serves as stop, and can then let go of the weight 50. Alternatively, or additionally to the formation of a stop (protrusion 56), which defines the fall height, e.g., one or several marks ("scale") can also be provided on the shaft of the needle 44 in order to thus provide for a lifting of the weight 50 to one or several fall heights, which are thus defined.

In the illustrated example, the piercing mechanism 42 further has a spring mechanism 58, which serves for to bias the needle 44 opposite to its piercing direction and which, in the illustrated example, is formed as a helical compression spring, which surrounds the shaft of the needle 44 and which is supported on the wall 46 on the one hand and on the radial protrusion 52 of the needle 44 on the other hand. The piercing process of the needle 44 can thus advantageously take place with a piercing depth, which can be reproduced in a well-defined manner, wherein the extent of this piercing depth is ultimately a function of the characteristic of the spring mechanism 58, of the fall height, and of the mass of the weight 50, and properties of the needle tip (material, geometry) in combination with properties of the crucible cover 16 to be pierced (e.g., material and thickness of a sealing layer to be pierced).

Deviating from the illustrated exemplary embodiment, the piercing mechanism 42 could also have, e.g., a mechanical stop for limiting the piercing depth of the needle 44.

It has turned out to be mostly advantageous in the context of the invention when the chamber cover 40, with its wall 46, forms a (dome-like) "hood part" (see, e.g., FIG. 4), so that the sample chamber 12 or in the region of the chamber opening 18, respectively, is expanded by attachment of the chamber cover 40 or, in the illustrated example, of the covering/piercing unit 40, 42, respectively. A gas outlet of the chamber cover 40 is preferably arranged in a distal region of the hood shape in this case (as is the case for the gas outlet 32 provided in the illustrated example).

In the illustrated example, the piercing mechanism 42 further has a mechanical centering mechanism 60 ("centering aid") by means of which the sample crucible 14 together with crucible cover 16 is centered with respect to the piercing mechanism 42 and thus the needle 44 before performing the piercing process. The piercing of the crucible cover 16 thus advantageously takes place at a well-defined location of the crucible cover 16.

In the illustrated example the centering mechanism 60 of the covering/piercing unit 40, 42 is formed by means of several centering jaws 62, which are arranged on the inside of the wall 46 and which are, e.g., formed in one piece with the wall 46, in such a way that they contact a jacket surface of the sample crucible 14 and/or a jacket surface of the crucible cover 16 when performing the piercing process, in order to thus force the sample crucible 14 together with the crucible cover 16 into a certain position with respect to the needle 44 (centering) before the hole is pierced into the crucible cover 16 of the sample crucible 14 by means of the needle 44.

In the illustrated example, the displaceable crucible receptacle furthermore has the advantage that the sample crucible 14 together with already punctured crucible cover 16 can be displaced from the first position into the second position before the covering/piercing unit 40, 42 is then removed from the chamber opening 18 of the sample chamber 12 in the second position and is replaced with the other chamber cover. Due to the fact that in the second position, the sample crucible 14 is located further on the bottom and thus further away from the chamber opening 18, at which a certain gas exchange between gas atmosphere and ambient air is unavoidable in practice after the removal of the covering/piercing unit 40, 42, the sample is even better protected against a contact with ambient air during this sample preparation phase (replacement of the chamber cover).

Figure 2:
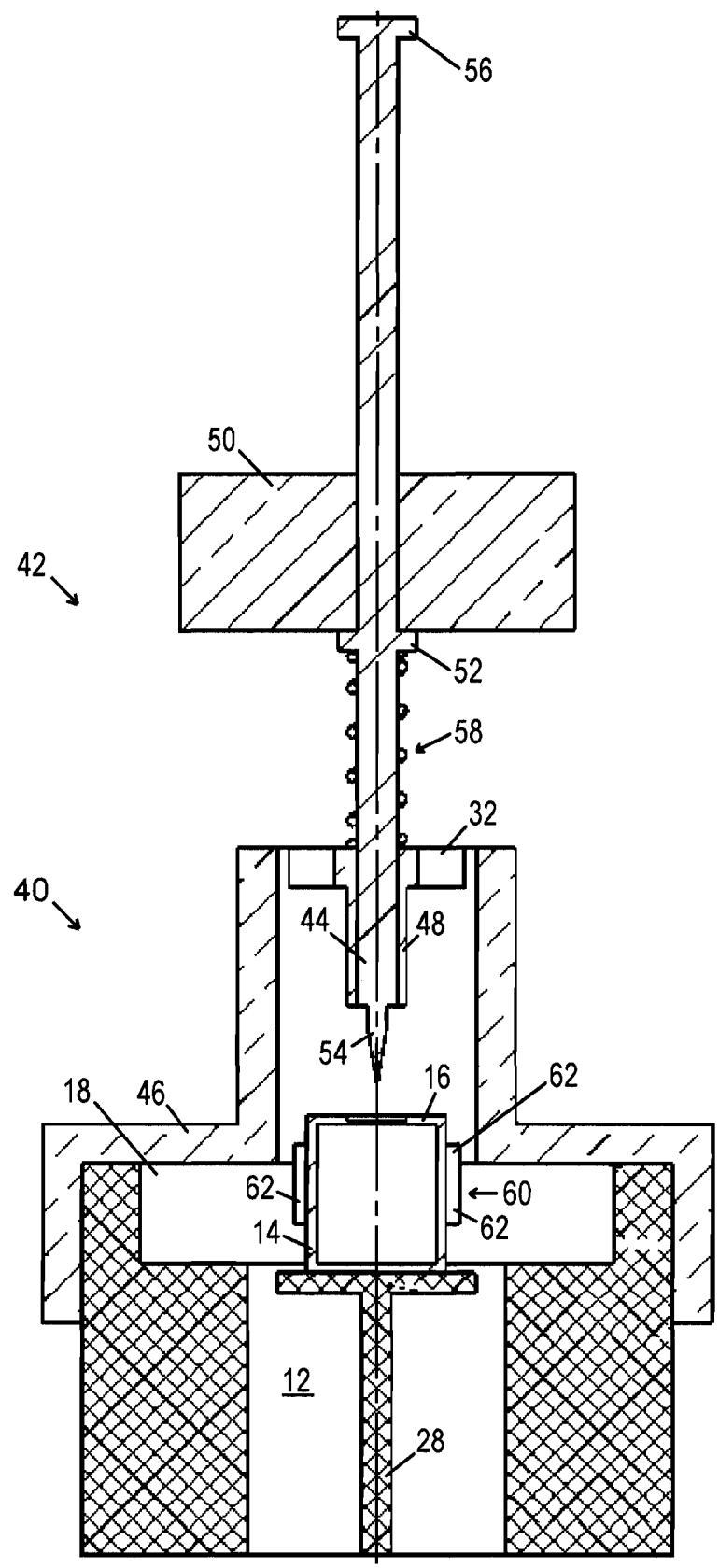
FIG. 2 shows a detail of the sectional view of FIG. 1, the illustration of which is slightly simplified, namely a covering/piercing unit of the device of FIG. 1.

FIG. 2 shows, in an enlarged manner and slightly schematically simplified, the covering/piercing unit 40, 42 from the sectional view of FIG. 1.

Figure 3:
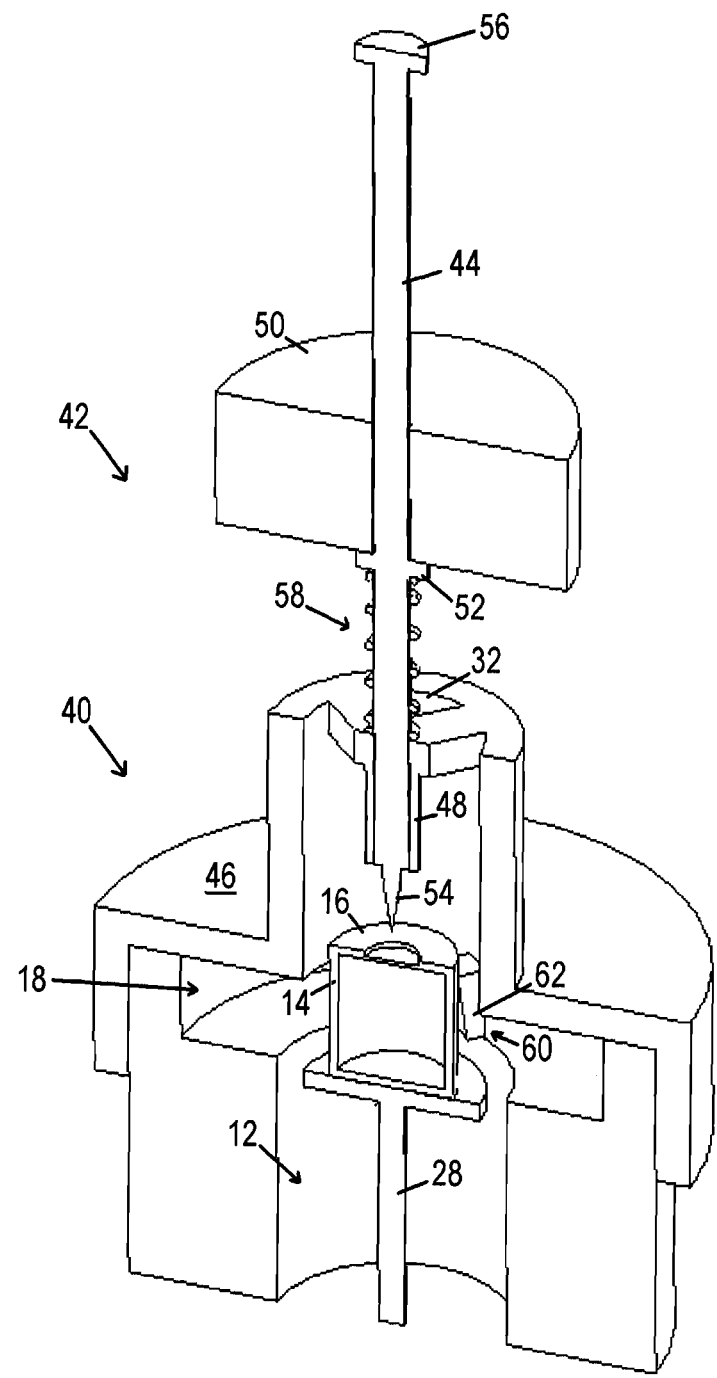
FIG. 3 shows a cut perspective view of the covering/piercing unit of FIG. 2.

FIG. 3 shows a cut perspective view of the covering/piercing unit 40, 42.

Figure 4:
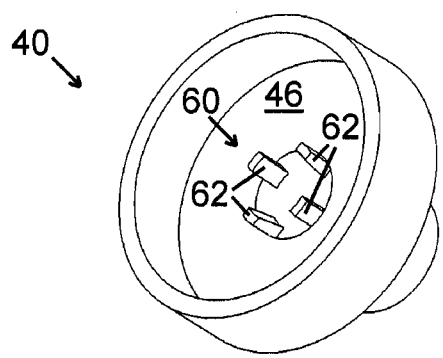
FIG. 4 shows a perspective view of a hood part of the covering/piercing unit of FIGS. 2 and 3.

FIG. 4 shows a perspective view of a "hood part" of the covering/piercing unit 40, 42 of FIGS. 2 and 3, comprising the wall 46 and the centering mechanism 60, which is formed by several centering jaws 62.

If, apart from the function of protecting an exchange of media and/or energy (heat) between sample chamber 12 and surrounding area (in FIG. 1 above the covering/piercing unit 40, 42) has a further function when performing the thermal analysis, it is advantageous when the covering/piercing unit 40, 42 is replaced with a chamber cover, which is optimized with regard to the mentioned further function(s), after piercing the hole into the crucible cover 16 and before performing the thermal analysis of the sample. Such a further function can be, e.g., to provide a carrier gas outlet, through which gas acting as carrier gas during the thermal analysis of the sample, together with gaseous components originating from the sample is transferred from the sample chamber 12 to an analysis mechanism (e.g., comprising a mass spectrometer).

In the illustrated exemplary embodiment, the device 10 thus has a (non-illustrated) further chamber cover, which, instead of the covering/piercing unit 40, 42, can be attached to the chamber opening 18 of the sample chamber 12, and which, similar to the gas outlet 32 of the covering/piercing unit 40, 42, has a gas outlet, to which a gas line leading to an analysis mechanism can be or is connected, respectively.

A method for a thermal analysis of the sample performed using the device 10 can in particular comprise the following steps:
   introducing the sample crucible 14, together with crucible cover 16 attached thereto and sample received therein into the sample chamber 12 through the chamber opening 18 of the sample chamber 12,
   attaching the covering/piercing unit 40, 42 to the chamber opening 18 of the sample chamber 12 and creating a gas atmosphere in the sample chamber 12 by means of the gas conveying mechanism 30, 31, 32,
   piercing a hole into the crucible cover 16 of the sample crucible 14 by means of the piercing mechanism 42 of the covering/piercing unit 40, 42,
   performing the thermal analysis of the sample by means of the temperature control mechanism 20 for controlling the temperature of the sample chamber 12 according to a predetermined temperature program (time-dependent temperature course) and the measuring mechanism for measuring the sample temperature and the mass change of the sample.

If the method for the thermal analysis of the sample thereby provides a time-dependent determination of the type and quantity of volatile decomposition products of the sample in the course of the respective temperature program by means of mass spectroscopy (MS) simultaneously to the thermogravimetry (TG), the covering/piercing unit 40, 42 is removed from the chamber opening 18 of the sample chamber 12 after piercing the hole into the crucible cover 16 but before performing the thermal analysis of the sample, and is replaced with another chamber cover, which has already been mentioned above, on which a gas outlet is formed, via which the volatile decomposition products of the sample are conveyed to a mass spectrometer during the thermal analysis.

A gas flowthrough of the sample chamber 12 is thereby effected by means of the gas conveying mechanism, in that the respective gas, which can also be referred to as carrier gas with respect to the function thereof in connection with the mass spectroscopy, is let in with a predetermined flow rate in the lower region of the sample chamber 12 on the gas inlet 30 and/or 31 and is let out towards the mass spectrometer in the upper region of the sample chamber 12 on the gas outlet of the chamber cover (optionally, e.g., via a separating column of a gas chromatography mechanism).

Such a gas flowthrough of the sample chamber 12 can similarly already be provided during phases of the sample preparation preceding the actual analysis, namely when introducing the sample crucible 14 into the sample chamber 12 as well as when removing the covering/piercing unit 40, 42 from the chamber opening 18 and following attaching of the other chamber cover to the chamber opening 18.

It is advantageous in this context that, as already described with reference to FIG. 1, the covering/piercing unit 40, 42 has the gas outlet 32, through which the gas, which flows into the sample chamber 12 via the gas inlet 30 of the device 10, can flow out of the sample chamber 12 to the outside into the environment when the covering/piercing unit 40, 42 is attached to the chamber opening 18. After attaching the covering/piercing unit 40, 42, air can thus be displaced quickly from the sample chamber 12 in an advantageous manner and can be replaced with the gas atmosphere ("protective gas atmosphere"), in which the opening of the crucible cover 16 can then take place (by piercing with the needle 44).

It is preferably provided hereby that the gas flowthrough of the sample chamber 12, which is effected by means of the gas conveying mechanism, is effected so that the flow rate thereof while introducing the sample crucible 14 into the sample chamber 12 and/or while replacing the covering/piercing unit 40, 42 with the other chamber cover is higher (e.g., at least by a factor of 2) than while performing the thermal analysis.

Returning to FIG. 1, a crucible receptacle comprising a deposit surface for depositing the sample crucible 14 thereon is formed in the case of the exemplary embodiment of the device 10 illustrated in FIG. 1 by means of the sample crucible carrier 28 or the upper end thereof in FIG. 1, respectively, wherein, in this example, a special characteristic is that this crucible receptacle can be displaced in the vertical direction between a first position shown in FIG. 1 for depositing the sample crucible 14 and for piercing the hole into the crucible cover 16, and a (non-illustrated) second position for performing the thermal analysis of the sample.

In this second position, the sample crucible 14 is located approximately in the center of the heating jacket 22 of the temperature control mechanism 20 for the purpose of performing the thermal analysis. The second position of the displaceable crucible receptacle or of the displaceable sample crucible carrier 28, respectively, is therefore provided further on the bottom than the first position shown in FIG. 1, i.e., further away from the chamber opening 18 and further inside the device 10.

In the first position, the introducing and depositing of the sample crucible 14, which is held, e.g., by means of a pair of tweezers, into the device 10 (through the chamber opening of the sample chamber 12) is simplified, whereas in the second position, a precise temperature control of the sample can be ensured during the thermal analysis.

In the illustrated example, the displaceable crucible receptacle furthermore has the advantage that a mechanical stress caused by piercing the hole into the crucible cover 16 of the sample crucible 14 is not transferred to the scale 26, which is provided in this example for the thermogravimetric analysis (TG). This is so because in the first position, the sample crucible carrier 28 is lifted upwards with the help of a lifting mechanism 70 and is thus mechanically decoupled from the scale 26. The sample crucible carrier 28 is lowered downwards with the help of the lifting mechanism 70 and is thus deposited on the scale 26 only after piercing the hole into the crucible cover 16 but before performing the thermal analysis.

In the illustrated example, the displaceable crucible receptacle furthermore has the advantage that the sample crucible 14 together with already punctured crucible cover 16 can be displaced from the first position into the second position, before, in the second position, the covering/piercing unit 40, 42 is then removed from the chamber opening 18 of the sample chamber 12 and is replaced with the other chamber cover. Due to the fact that in the second position, the sample crucible 14 is located further on the bottom and thus further away from the chamber opening 18, at which a certain gas exchange between gas atmosphere and ambient air is unavoidable in practice after the removal of the covering/piercing unit 40, 42, the sample is even better protected against a contact with ambient air during this sample preparation phase (replacement of the chamber cover).

Due to the fact that the crucible receptacle (sample crucible carrier 28), which can be displaced between the first position and the second position, is formed in the illustrated exemplary embodiment, the method performed by means of the device 10 can thus provide in an advantageous manner that the introduction of the sample crucible 14 into the sample chamber 12 takes place by depositing the sample crucible 14 onto a deposit surface of the crucible receptacle provided on the upper end of the sample crucible carrier 28 when the crucible receptacle is in the first position, that after the chamber cover (in the example: covering/piercing unit 40, 42) is attached to the chamber opening 18 of the sample chamber 12 and after a defined gas atmosphere (and preferably gas flowthrough) is created in the sample chamber 12, the piercing of the hole into the crucible cover 16 takes place when the crucible receptacle is in the first position, that after piercing the hole into the crucible cover 16 and before performing the thermal analysis of the sample, a displacement of the crucible receptacle from the first position into the second position takes place.

In the following description of further exemplary embodiments, the same reference numerals are used for components, which act in the same way, in each case supplemented by a lowercase letter to differentiate the embodiment. Essentially only the differences compared to the already-described exemplary embodiment(s) will thereby be addressed, and, apart from that, reference is hereby expressly made to the description of preceding exemplary embodiments.

An exemplary embodiment of a sample crucible 14a comprising a crucible cover 16a, which can be used in a particularly advantageous manner in the context of the invention, will be described below with reference to FIGS. 5 to 7.

Figure 5:
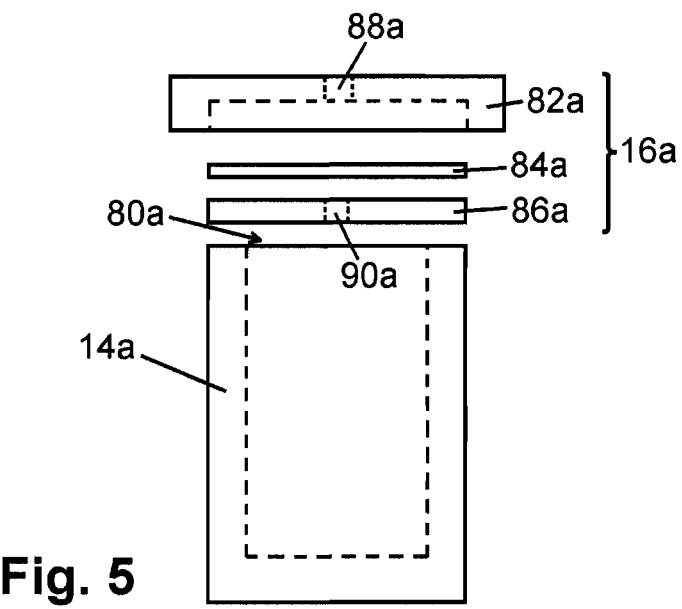
FIG. 5 shows a schematic exploded view of a sample crucible comprising a crucible cover according to an exemplary embodiment.

FIG. 5 shows the sample crucible 14a comprising crucible cover 16a in a schematic exploded view from the side.

The sample crucible 14a has a cylindrical shape comprising an interior for receiving the sample and comprising a crucible opening 80a on an upper front side of this cylindrical shape.

In the illustrated example, the crucible cover 16a, which can be or is attached to the sample crucible 14a at the crucible opening 80a of the sample crucible 14a consists of a cap 82a, a pierceable sealing layer 84a (sealing film), and a stabilizing layer 86a.

The cap 82a is formed as a screw cap and can be circumferentially connected (here: screwed-connected) on its circumferential region to an opening edge of the sample crucible 14a. In the example, the cap 82 has, on its circumferential edge region, an internal thread, which can be screw-connected to a corresponding external thread of the sample crucible 14a. In addition, the cap 82a has a cap hole 88a, which is arranged in the center, and which penetrates the cap 82a.

In the mounted state of the "sample crucible/crucible cover combination" 14a, 16a, the pierceable sealing layer 84a is arranged on the inside of the cap 82a and serves the purpose of sealing the interior of the sample crucible 14a in this state.

In the mounted state, the stabilizing layer 86a is arranged on the inside of the pierceable sealing layer 84a. In addition, the stabilizing layer 86a has a stabilizing layer hole 90a, which is arranged coaxially to the cap hole 88a, and which penetrates the stabilizing layer 86a.

In the mounted state of the sample crucible/crucible cover combination 14a, 16a, an edge of the two-layer structure of sealing layer 84a and stabilizing layer 86a arranged therebelow is clamped circumferentially between the cap 82a and the sample crucible 14a.

In the illustrated example, the sample crucible 14a is made in one piece (bottom and jacket) of steel, wherein the surfaces limiting the interior are coated with a gold alloy. In the illustrated example, the crucible cover 16a consists of steel (cap 82a) and a gold alloy (sealing layer 84a and stabilizing layer 86a).

In the case of the sample crucible 14a comprising crucible cover 16a, the piercing of a hole into the crucible cover 16a can advantageously take place in such a way that the needle used for this purpose (e.g., needle 44 in FIGS. 1 to 4) passes through the cap hole 88a and then pierces the sealing layer 84a located therebelow. A mechanical support for the sealing layer 84a is thereby advantageously created by means of the stabilizing layer 86a, so that when piercing the hole into the sealing layer 84a, the latter cannot move back when being stressed by the needle and a well-defined and reproducible geometry of the hole is thus attained. By providing the stabilizing layer hole 90a, it is advantageously avoided that the piercing movement of the needle is impeded by the stabilizing layer 86a.

Figure 6:
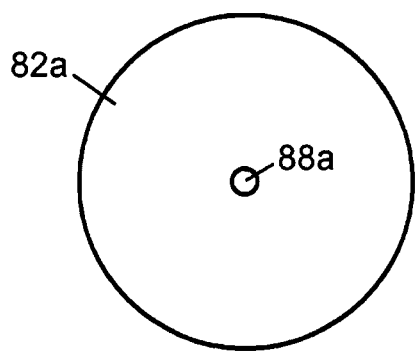
FIG. 6 shows a top view of a cap of the crucible cover of FIG. 5.

FIG. 6 shows a top view of the cap 82a of the crucible cover 16a.

Figure 7:
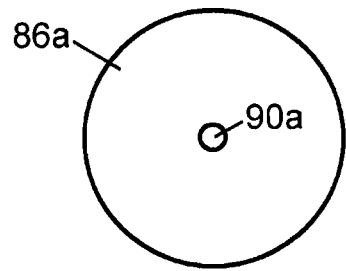
FIG. 7 shows a top view of a stabilizing layer of the crucible cover of FIG. 5.

FIG. 7 shows a top view of the stabilizing layer 86a of the crucible cover 16a.

The diameters of the cap hole 88a and of the stabilizing layer hole 90a on the one hand and of the needle on the other hand are to be selected adapted to one another so that the needle or at least a tip of the needle, respectively, fits through the cap hole 88a and preferably also through the stabilizing layer hole 90a. In the illustrated example, the diameters of the cap hole 88a and of the stabilizing layer hole 90a are of equal dimension and are each approx. 0.5 mm.

Figure 8:
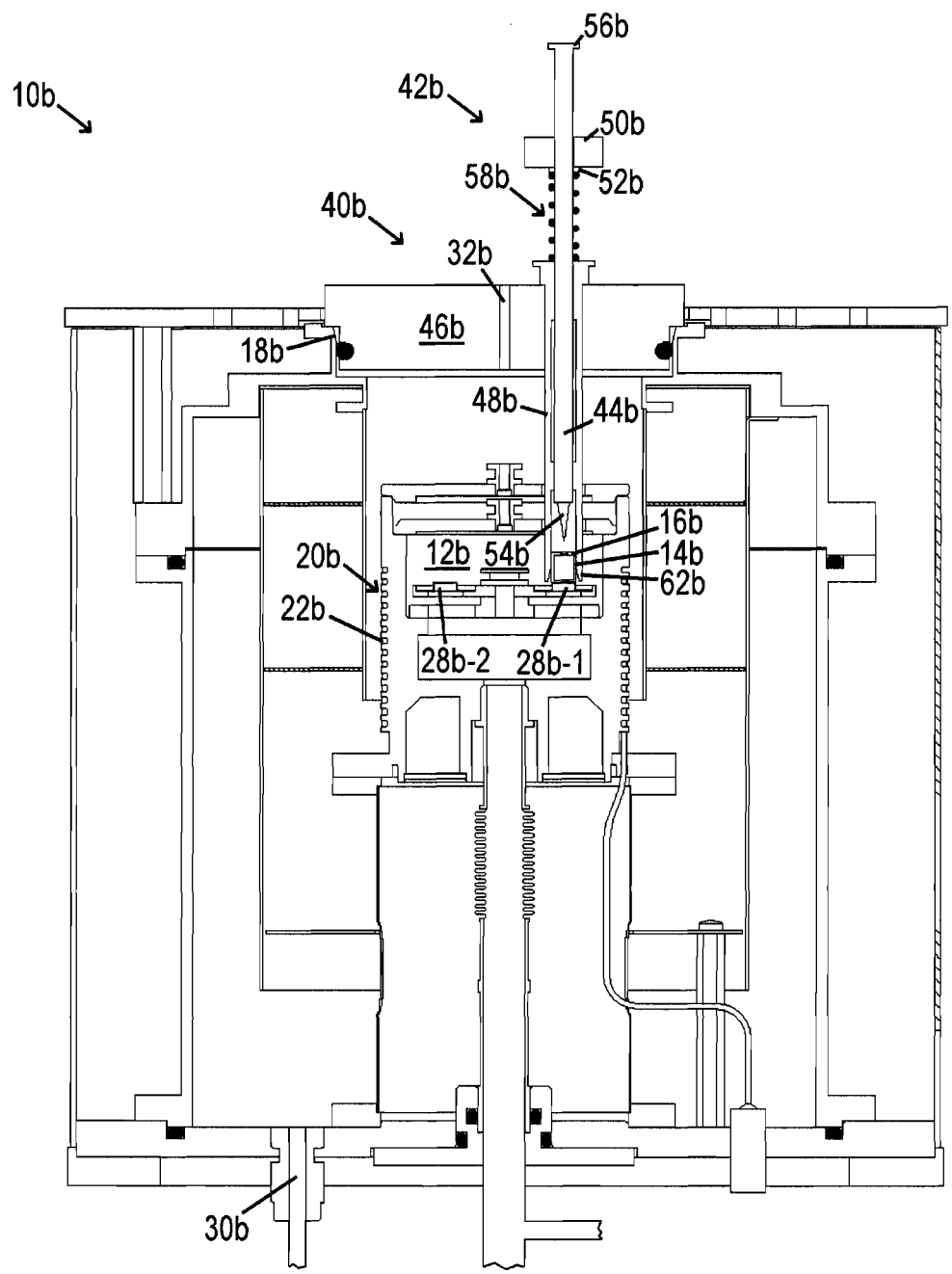
FIG. 8 shows a sectional view of a device for a thermal analysis of a sample according to a further exemplary embodiment.

FIG. 8 shows a further exemplary embodiment of a device 10b for a thermal analysis of a sample. As does the device 10, which has already been described with regard to FIG. 1, the device 10b has a sample chamber 12b for receiving a sample crucible 14b comprising a crucible cover 16b attached thereto, wherein the sample to be analyzed is located in the interior of the sample crucible 14b. In an upper region of the device 10b, the sample chamber 12b has a chamber opening 18b, through which the sample crucible 14b can be introduced into the sample chamber 12b to prepare the analysis. The device 10b further has a temperature control mechanism 20b, by means of which the temperature of the sample chamber 12b is controlled during the analysis of the sample according a predetermined temperature program, in the course of which a chamber temperature in the interior of the sample chamber 12b is changed and a sample temperature and additionally one or several further measured variables relating to properties of the sample are measured by means of a measuring mechanism of the device 10b.

In contrast to the device 10 of FIG. 1, the device 10b is formed for performing a thermal analysis of the sample comprising the method of the differential scanning calorimetry (DSC).

In this case, two sample crucible carriers 28b-1, 28b-2 (equipped with thermal elements for the temperature measurement), which act as "sensors" on which a sample crucible of the described type can in each case be deposited, are provided in the sample chamber 12b. When performing the DSC, both sample crucibles are simultaneously or optionally also two samples (e.g., "actual sample" and "reference sample"), respectively, and are also simultaneously subjected to a common temperature control in the sample chamber 12b. Alternatively to the simultaneous temperature control of two samples, the second crucible can, e.g., also be used "empty" (i.e. without sample or reference sample, respectively, stored therein) during the method.

The measuring mechanism of the device 10b thus comprises a temperature measuring mechanism for measuring the temperatures of the actual sample (in the sample crucible 14b) as well as of the refence sample (or of an "empty" second sample crucible, respectively).

In the use situation of the device 10b, each of the sample crucible carriers 28b-1, 28b-2 serves the purpose of being able to arrange a sample crucible, such as, e.g., the illustrated sample crucible 14b, thereon, in order to thus arrange the sample crucible together with optionally sample (including "reference sample") in the sample chamber 12b in a defined manner, and for the purpose of measuring a temperature on the bottom side of the respective crucible or thus the sample temperature (in the case of the crucible 14b containing the sample), respectively. For this purpose, a thermal element (not illustrated in the figure) is arranged on the surface or in the interior of each sample crucible carrier 28b-1, 28b-2.

In the case of the differential scanning calorimetry performed by means of the device 10b, in particular a time-dependent course of a difference of the temperatures measured by means of the two sensors (sample crucible carriers 28b-1, 28b-2) is determined as part of the evaluation of a measuring result (measuring data), in particular in order to be able to determine energetic effects and/or, e.g., a temperature-dependent specific heat capacity of the sample therewith. In a (non-illustrated) further development of the device 10b, for example a combination of the DSC with at least one further thermoanalytical method, such as in particular, e.g., a TG (thermogravimetric analysis) could also be provided.

As in the case of the device 10, which has already been described further above (FIG. 1), a chamber cover 40b and the piercing mechanism 42b in the case of the device 10b (FIG. 8) are also formed to be structurally combined as a covering/piercing unit 40b, 42b, which, in turn, has a wall 46b, a guide bearing 48b formed thereon, and a needle 44b movably stored therein.

In contrast to the device 10 (FIG. 1), however, the guide bearing 48b and thus the needle 44b in the case of the device 10b (FIG. 8), in adaptation on the "eccentric" position of the crucible cover 16b of the sample crucible 14b to be pierced, is not arranged in the center of the (e.g., circular) chamber cover 40b, but eccentrically.

In summary, the invention and the described exemplary embodiments make it possible to introduce a sample crucible, which is closed in an air-tight manner, into a device for a thermal analysis of a sample under protective gas conditions, and to open it only there under protective gas conditions. As part of the sample preparation, the risk of a change of the sample as a result of unwanted chemical or physical reactions with components of the ambient air is thus drastically reduced in an advantageous manner.

The invention claimed is:

1. A device for a thermal analysis of a sample, having
    a sample chamber for receiving a sample crucible comprising a crucible cover attached thereto, in the interior of which a sample to be analyzed is located, wherein the sample chamber has a chamber opening for introducing the sample crucible into the sample chamber,
    a temperature control mechanism for controlling the temperature of the sample chamber,
    a measuring mechanism for measuring a temperature of the sample and one or several further measured variables,
    a gas conveying mechanism for creating a gas atmosphere in the sample chamber,
    a chamber cover, which can be attached to the chamber opening of the sample chamber,
    a piercing mechanism equipped with a needle, which is suitable to pierce a hole into the crucible cover of the sample crucible by means of the needle when the sample crucible is received in the sample chamber and when the chamber cover is attached to the chamber opening.

2. The device according to claim 1, wherein the chamber cover and the piercing mechanism are formed to be structurally combined as a covering/piercing unit.

3. The device according to claim 2, wherein the device has another chamber cover, which can be attached to the chamber opening of the sample chamber when the covering/piercing unit is detached from the chamber opening.

4. The device according to claim 2, wherein the covering/piercing unit has:
    a wall provided for covering the chamber opening,
    a guide bearing formed on the wall for movably storing the needle, wherein the needle can extend from an inside of the wall, which faces the sample chamber when the covering/piercing unit is attached, through the wall, to an outside of the wall, which faces away from the sample chamber when the covering/piercing unit is attached.

5. The device according to claim 1, wherein the piercing mechanism has a mechanical stop for limiting a piercing depth of the needle.

6. The device according to claim 1, wherein the piercing mechanism has a mechanical centering mechanism for centering the sample crucible together with the crucible cover with respect to the needle.

7. The device according to claim 1, wherein a crucible receptacle comprising a deposit surface for depositing the sample crucible thereon is formed in the sample chamber, and wherein the crucible receptacle can be displaced between a first position for depositing the sample crucible and piercing a hole into the crucible cover, and a second position for performing the thermal analysis of the sample.

8. A method for a thermal analysis of a sample, which is located in the interior of a sample crucible having a crucible cover attached thereto, including the steps of:
    introducing the sample crucible into a sample chamber through a chamber opening of a sample chamber,
    attaching a chamber cover to the chamber opening of the sample chamber and creating a gas atmosphere in the sample chamber with a gas conveying mechanism,
    piercing a hole into the crucible cover of the sample crucible with a piercing mechanism,
    performing the thermal analysis of the sample with a temperature control mechanism for controlling the temperature of the sample chamber and a measuring mechanism for measuring a temperature of the sample and one or several further measured variables.

9. The method according to claim 8, wherein the chamber cover and the piercing mechanism are formed to be structurally combined as a covering/piercing unit, and wherein the covering/piercing unit is removed from the chamber opening of the sample chamber after piercing the hole into the crucible cover and before performing the thermal analysis of the sample and is replaced with another chamber cover.

10. The method according to claim 9, wherein the creation of the gas atmosphere is realized by means of a gas flow-through of the sample chamber, which is effected by means of the gas conveying mechanism and the flow rate of which is higher while replacing the covering/piercing unit with the other chamber cover than while performing the thermal analysis.

11. A sample crucible comprising crucible cover, for use for a device including:
    a temperature control mechanism for controlling the temperature of the sample chamber,
    a measuring mechanism for measuring a temperature of the sample and one or several further measured variables,
    a gas conveying mechanism for creating a gas atmosphere in the sample chamber,
    a chamber cover, which can be attached to the chamber opening of the sample chamber,
    a piercing mechanism equipped with a needle, which is suitable to pierce a hole into the crucible cover of the sample crucible by means of the needle when the sample crucible is received in the sample chamber and when the chamber cover is attached to the chamber opening.

12. The sample crucible comprising crucible cover according to claim 11, wherein the crucible cover further has:
    a stabilizing layer arranged on the inside of the sealing layer comprising a stabilizing layer hole, which is formed coaxially to the cap hole therein.

13. A covering/piercing unit for a device for a thermal analysis of a sample, wherein the device has a sample chamber for receiving a sample crucible including a crucible cover attached thereto, in the interior of which a sample to be analyzed is located, and wherein the sample chamber has a chamber opening for introducing the sample crucible into the sample chamber, wherein the covering/piercing unit has:
    a wall provided for covering the chamber opening,
    a guide bearing formed on the wall,
    a needle, which is movably stored by means of the guide bearing and which extends from an inside of the wall facing the sample chamber when the covering/piercing unit is attached, through the wall, to an outside of the wall facing away from the sample chamber when the covering/piercing unit is attached.

14. The thermal analysis method of claim 8 further comprising use of a mechanism including:
    a temperature control mechanism for controlling the temperature of the sample chamber,
    a measuring mechanism for measuring a temperature of the sample and one or several further measured variables,
    a gas conveying mechanism for creating a gas atmosphere in the sample chamber,
    a chamber cover, which can be attached to the chamber opening of the sample chamber,
    a piercing mechanism equipped with a needle, which is suitable to pierce a hole into the crucible cover of the sample crucible by means of the needle when the sample crucible is received in the sample chamber and when the chamber cover is attached to the chamber opening.

15. The sample crucible of claim 11 further comprising:
    an approximately cylindrical shape having an interior for receiving the sample and having an opening,
    a crucible cover which can be attached to the sample crucible opening,
    a hole included in the crucible cover and wherein the crucible cover can be screwed to the sample crucible, and
    a pierceable sealing layer arranged on an inside of the crucible cover which seals the interior of the sample crucible.

* * * * *